United States Patent [19]
Strober et al.

[11] Patent Number: 5,853,697
[45] Date of Patent: Dec. 29, 1998

[54] METHODS OF TREATING ESTABLISHED COLITIS USING ANTIBODIES AGAINST IL-12

[75] Inventors: Warren Strober; Ivan Fuss, both of Bethesda, Md.; Markus Neurath, Mainz, Germany

[73] Assignee: The United States of America, as represented by the Department of Health & Human Services, Washington, D.C.

[21] Appl. No.: 547,979

[22] Filed: Oct. 25, 1995

[51] Int. Cl.$^6$ .......... A61K 39/395; C07K 16/24; C12P 21/08; G10N 33/543
[52] U.S. Cl. .......... 424/9.2; 424/158.1; 435/6; 435/7.91; 435/7.94; 435/91.2; 436/63; 436/87; 436/811; 530/388.23; 530/389.2
[58] Field of Search .......... 530/388.23, 389.2; 424/130.1, 145.1, 158.1, 9.2; 436/63, 87, 811, 815; 435/6, 7.91, 7.94, 91.2

[56] References Cited

U.S. PATENT DOCUMENTS 5,547,852  8/1996  Kseiler et al. .

FOREIGN PATENT DOCUMENTS

| 0 433 827 A2 | 12/1990 | European Pat. Off. . |
| 0 621 341 A2 | 4/1994 | European Pat. Off. ........ C12P 21/08 |
| 0640689 A | 3/1995 | European Pat. Off. . |
| WO 90/05147 | 5/1990 | WIPO . |
| WO 95/01997 | 1/1995 | WIPO . |
| WO 95/23865 | 9/1995 | WIPO . |
| WO 95/24918 | 9/1995 | WIPO . |

OTHER PUBLICATIONS

Trembleau et al. The role of IL–12 in the induction of organ–specfic autoimmune disease *Immunol. Today* 16(8):383–386, 1995.
Powrie, F. et al. Therapeutic Immunol. 2 (2): 115–123, Apr. 1995.
Fretland, D. J. et al. J. Pharmacology and Experimental Therap. 225 (2): 572–576, Nov. 1990.
Leonard. J. P. et al. J. Exp. Med. 181 (1): 381–386, Jan. 1995.
Marcus, A. J. et al. J. Pharm. Pharmacol. 41 (6): 423–426, Jun. 1989.
Rask–Madsen, J. et al. Agents and Actions Spec. No. C37–46, 1992.
Sharon, P. et al. Gastroenterology 88 (1 Pt 1): 55–63, Jan. 1985.
Banic, M. et al. Alimentary Pharmacology and Therapeutics 7 (2): 201–206, Apr. 1993.
Schoenhaut, D. et al. J. Immunol. 148: 3433–3440, Jun. 1, 1992.
Brunda, M. J. Leukocyte Biol. 55: 280–288, Feb. 1994.
Harris, E. et al. TIBTECH 11:42–44, Feb. 1993.
Derkx, B. et al. Lancet 342: 173–174, Jul. 17, 1993.
Duchmann, R. et al. Immunol. Microbio. and Inflammatory Disorders Abstracts A693, Apr. 1993.
Strober, W. et al. Cell 75: 203–205, Oct. 22, 1993.
D'Andrea, A. et al. J. Exp. Med. 178: 1041–1048, Sep. 1993.
Wysocka et al. "Interleukin–12 is required for interferon–γ production and lethality in . . . " *Eur. J. Immounl.* 25:672–676, 1995.
Van Dullemen et al. "Treatment of Crohn's Disease with Anti–Tumor Necrosis Factor Chimeric Monoclonal Antibody (cA2)" *Gastroenterol.* 109:129–135, Jul. 1995.
Leonard et al. "Prevention of Experimental Autoimmune Encephalomyelitis by Antibodies Against Interleukin 12" Brief Definitive Report *J. Exp. Med.* 181:381–386, Jan. 1995.
Murray, Henry W. and Hariprashad, Jun. "Interleukin 12 is Effective Treatment for an Established Systemic Intracellular Infection: Experimental . . . " Brief Definitive Report *J. Exp. Med.* 181: 387–391, Jan. 1995.
Ling et al. "Human IL–12 p40 Homodimer Binds to the IL–12 Receptor but Does not Mediate Biologic Activity" *J. of Immunol.* 154:116–127, 1995.
Trinchieri, Giorgio "Interleukin–12: A Cytokine Produced by Antigen–Presenting Cells with Immunoregulatory Functions in the Generation of T–Helper Cells Type 1 . . . " *Blood* 84(12):4008–4027, Dec. 15, 1994.

(List continued on next page.)

*Primary Examiner*—Frank C. Eisenschenk
*Assistant Examiner*—Evelyn Rabin
*Attorney, Agent, or Firm*—Needle & Rosenberg, P.C.

[57] ABSTRACT

The present invention provides a method for treating the inflammatory response of an established colitis in a subject with inflammatory bowel disease (IBD), comprising administering to a subject diagnosed with an established colitis from an IBD an amount of an antibody to interleukin-12 effective in reducing the colitis-inducing effect of interleukin-12. Also provided is a method for screening a substance for its effectiveness in reducing the inflammatory response of an established colitis comprising obtaining an animal having an established colitis; administering the substance to an animal; and assaying the animal for an effect on interleukin-12 which results in the reduction of the inflammatory response of the colitis, an amount of reduction of the inflammatory response greater than the amount of reduction produced by the administration of antibodies against interferon-gamma or tumor necrosis factor-alpha indicating an effective substance. Additionally, the present invention provides a method for screening a substance for its effectiveness in preventing inflammatory bowel disease comprising administering the substance to an animal susceptible to colitis; subjecting the animal to a treatment that will induce a colitis; assaying the animal for the development of a colitis; and comparing the effectiveness of the substance in preventing development of a colitis to the effectiveness of antibodies to interferon-gamma or tumor necrosis factor-alpha in preventing development of a colitis, a substance more effective in preventing the development of a colitis than antibodies to interferon-gamma or tumor necrosis factor-alpha indicating an effective substance.

11 Claims, 1 Drawing Sheet

OTHER PUBLICATIONS

Powrie et al. "Inhibition of Th1 Responses Prevents Inflammatory Bowel Disease in scid Mice Reconstituted with CD45RB$^{hi}$ CD4+ T Cells" *Immunity* 1:553–562, Oct 1994.

Kubin et al. "Interleukin 12 Synergizes with B7/CD28 Interaction in Inducing Efficient Proloferation . . . " *J. Exp. Med.* 180–:211–222, Jul. 1994.

Wynn et al. "Endogenous Interleukin 12 (IL–12) Regulates Granuloma Formation Induced by Eggs of *Schistosoma mansoni* and Exogenous IL–12 . . . " *J. Exp. Med.* 179:1551–1561, May 1994.

Powrie et al. "Regulatory Interactions between CD45RB$^{high}$ and CD45RB$^{low}$ CD4+ T Cells are Important for he Balance between . . . " *J. Exp. Med.* 179:589–600, Feb. 1994.

Seder et al. "Interleukin 12 Acts Directly on CD4+ T Cells to Enhance Priming for Interferon γ Production and Diminishes Interleukin 4 Inhibition . . . " *Proc.Natl. Acad. Sci Usa* 90:10188–10192, Nov. 1993.

Strober, Warren and Ehrhardt, Rolf "Chronic Intestinal Inflammation: An Unexpected Outcome in Cytokine or T Cell Receptor Mutant Mice" *Cell* 75:205–205, Oct. 22, 1993.

Mombaerts et al. "Spontaneous Development of Inflammatory Bowel Disease in T Cell Receptor Mutant Mice" *Cell* 75:275–282, Oct. 22, 1993.

Duchmann et al. "Interleukin–12 mRNA is Induced in Lamina Propria Monoculear Cells from Patients with Inflammatory Bowel Disease (IBD)" *Immumol., Microbiol. and Inflammatory Disorders* Abstract A693. Apr. 1993.

Kühn et al. "Interleukin–10–Deficient Mice Develop Chronic Enterocolotis" *Cell* 75:263–274, Oct. 22, 1993.

Sadlack et al. "Ulcerative Colitis–like Disease in Mice with a Disrupted Interleukin–1 Gene" *Cell* 75:253–261, Oct. 22, 1993.

Kulkarni et al. "Transforming Growth Factor $\beta_1$ Null Mutation in Mice Causes Excessive Inflammatory Response and Early Death" *Proc. Natl. Acad. Sci. USA* 90:770–774, 1993.

Podlaski et al. "Molecular Characterization of Interleukin 12" *Archives and Biochem. and Biophysics* 294(1):230–237, Apr. 1992.

Morris et al. "Hapten–Induced Model of Chronic Inflammation and Ulceration in the Rat Colon" *Gastroenterol.* 96:795–803, 1989.

METHODS OF TREATING ESTABLISHED COLITIS USING ANTIBODIES AGAINST IL-12

BACKGROUND OF THE INVENTION

1. Field of the Invention

The present invention relates to a method of treating the established colitis of an inflammatory bowel disease by inhibiting the colitis-inducing effects of the cytokine interleukin-12 (IL-12). In particular, the present invention provides a method for treating an established colitis, especially by administering antibodies against IL-12. Further provided is a method for screening substances for their effectiveness in reducing the inflammatory response of an established colitis and preventing inflammatory bowel disease in a mouse model.

2. Background Art

Inflammatory bowel disease (IBD), encompassing Crohn's disease (CD) and ulcerative colitis (UC), are idiopathic chronic diseases occurring with increasing frequency in Western populations (1, 2). Recently, various animal models of chronic intestinal inflammation have been established which will likely provide new insights into the pathogenesis of IBD (3). These include mice carrying transgenes of HLA-B27 and β2-microglobulin (4) and mice in which the genes for interleulin-2 (IL-2) (5), interleukin-10 (IL-10) (6) and the alpha or beta chain of the T cell receptor (7) have been inactivated by homologous recombination. In addition, a colitis model has been recently established by the adoptive transfer of normal CD45RBhi T cells from BALB/c mice to C.B.-17 scid mice wherein the transferred T cells manifest a Th1 cytokine response associated with granulomatous inflammation. This experimental colitis can be prevented by systemic administration of anti-interferon-gamma (anti-IFN-γ) (two doses) and by systemic, daily administration of recombinant IL-10 (rIL10), given at the same time disease is induced, but not with recombinant interleukin-4 (rIL4) (8). However, treatment of established IBD using these methodologies was not suggested. The observation that administration of IL-10, a product of Th2 cell differentiation, but not IL-4, which is also a product of Th2 cell differentiation, can prevent experminental colitis underscores the unpredictability of administering cytolines to prevent or treat IBD.

IL-12 is a recently characterized cytokine with unique structure and pleiotropic effects (9–12). It consists of two disulfide-linked subunits, p40 and p35, that form functionally active p40/p35 heterodimers or inhibitory p40 homodirners. IL-12 is produced mainly by macrophages/monocytes and can be efficiently induced by intracellular parasites, bacteria and bacterial products. Functional studies have shown that IL-12 enhances cytolytic activity of natural killer (NK) cells and macrophages and induces, in synergism with the B7/CD28 interaction, cytokine production and proliferation of activated NK cells and T cells (13). Furthermore, IL-12 plays a pivotal role in Th1 T cell differentiation and induces naive T cells to produce IFN-γ. As a result of this ability to drive T cell responses to the Th1 phenotype, IL-12 has been shown to be an effective treatment of established parasitic infections in mice (14, 15), which elicit a Th2 T cell response. While antibodies to IL-12 have been shown to be useful in preventing experimental autoimmune encephalitis, a disease mediated by Th1 T cells (16), these results have not been extended to the treatment of established autoimmune encephalitis.

It has been shown that antibodies to tumor necrosis factor-alpha (TNF-α) have been employed in the treatment of CD (29). In this uncontrolled study, acute exacerbations of CD were blunted, however, patients remained steroid-dependent and disease invariably recurred within a several month period.

The present invention provides an effective treatment for IBD that is surprisingly more effective than existing therapies. The present invention further provides a method for screening for substances effective in their ability to inhibit the colitis-inducing effect of IL-12.

SUMMARY OF THE INVETON

The present invention provides a method for treating the inflammatory response of an established colitis in a subject with IBD, comprising administering to a subject diagnosed with an established colitis from an IBD an amount of an antibody to interleukin-12 effective in reducing the colitis-inducing effect of interleukin-12.

Also provided is a method for screening a substance for its effectiveness in reducing the inflammatory response of an established colitis comprising obtaining an animal having an established colitis; administering the substance to an animal; and assaying the animal for an effect on interleukin-12 which results in the reduction of the inflammatory response of the colitis, an amount of reduction of the inflammatory response greater than the amount of reduction produced by the administration of antibodies against IFN-γ or TFN-α indicating an effective substance.

Additionally, the present invention provides a method for screening a substance for its effectiveness in preventing inflammatory bowel disease comprising administering the substance to an animal susceptible to colitis; subjecting the animal to a treatment that will induce a colitis; assaying the animal for the development of a colitis; and comparing the effectiveness of the substance in preventing development of a colitis to the effectiveness of antibodies to interferon-gamma or tumor necrosis factor-alpha in preventing development of a colitis, a substance more effective in preventing the development of a colitis than antibodies to interferon-gamma or tumor necrosis factor-alpha indicating an effective substance.

DESCRIPTION OF THE PREFERRED EMBODIMENTS

Figure 1:
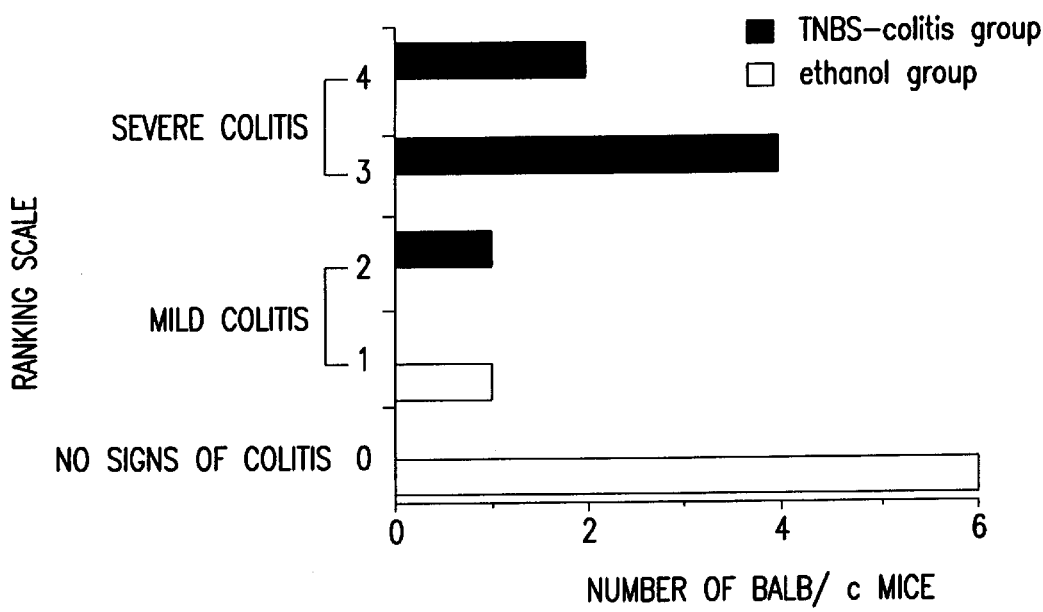
FIG. 1 shows the results of the histologic grading of colon sections from control BALB/c mice treated with ethanol (open bars) and from mice treated with TNBS (solid bars). Colon specimens were taken at indicated time points after administration of TNBS or ethanol and the magnitude of inflammatory changes in the colons was analyzed on HE-stained cross colon sections. Data were pooled from three independent experiments in each group.

The present invention may be understood more readily by reference to the following detailed description of specific embodiments and the Examples included herein.

This invention provides a method for treating the inflammatory response of an established colitis in a subject with IBD comprising administering to a subject diagnosed with an established colitis an amount of an antibody to IL-12 effective in reducing the colitis-inducing effect of IL-12. Any animal which is subject to colitis can be treated by this method although humans are the primary therapeutic target. As used herein, an "established colitis" refers to a condition of the colon characterized by a state of inflammation in which one or more of the following histological characteristics are detectable: leukocyte infiltration; thickening of the colon wall; transmural infiltrations; loss of goblet cells; ulcerations; granulomas; and fibrosis. Clinical symptoms can include, but are not limited to, diarrhea, rectal prolapse, weight loss, abdominal pain, dehydration and splenomegaly.

Antibodies to IL-12 can be from any source. However, to reduce the immunogenicity of the immunoglobulins themselves, antibodies are preferably of human origin or are antibodies generated in other species and "humanized" for administration in humans as described in Example VI. Fragments of antibodies which maintain IL-12 binding activity as well as fragments of IL-12 which maintain IL-12 binding activity (e.g., homodimer formation) and reduce the colitis-inducing effects of IL-12 are included within the meaning of the term "antibody." Such antibodies and fragments can be made by techniques known in the art and screened for specificity and activity according to the methods set forth in the Examples herein. For example, general methods for producing antibodies can be found in Harlow and Lane (23).

In the present invention, the antibody to IL-12 can be orally or parenterally administered in a pharmaceutically acceptable carrier to human subjects. Suitable carriers for use in the present invention include, but are not limited to, pyrogen-free saline. For parenteral administration of the antibodies, a sterile solution or suspension is prepared in saline that may contain additives, such as ethyl oleate or isopropyl myristate, and can be injected, for example, into subcutaneous or intramuscular tissues.

Alternatively, the antibodies may be microencapsulated with either a natural or a synthetic polymer into microparticles 4–8 μm in diameter, which target intestinal lymphoid tissues and produce a sustained release of antibody for up to four weeks (22, 28).

For treatment of humans, antibodies to IL-12, in soluble form, would typically be administered in a single dosage of between 10 mg and 20 mg/kg of body weight. Alternatively, patients can be given 10 mg to 20 mg/kg of body weight weekly until colitis symptoms subside. For oral administration, 500 mg to 1000 mg can be given P.O. For parenteral administration, 10 mg to 20 mg/kg of body weight can be administered as a single or as a weekly intravenous injection. However, the age, weight and condition of the individual must be considered in determining a final dose. For administration of antibodies to IL-12 in particulate form, 500 mg to 1000 mg can be microencapsulated as described for slow release over a four to eight week period. One skilled in the art will realize that dosages are best optimized by the practicing physician and methods for determining dosages are described for example, in *Remington's Pharmaceutical Sciences* (24).

Suitable carriers for oral administration of antibodies to IL-12 include one or more substances which may also act as flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pharmaceutically accepted oils, or a mixture of both. The liquid can also contain other suitable pharmaceutical additions such as buffers, preservatives, flavoring agents, viscosity or osmoregulators, stabilizers or suspending agents. Examples of suitable liquid carriers include water with or without various additives, including carboxypolymethylene as a pH-regulated gel. The antibodies may be contained in enteric coated capsules that release antibodies into the intestine to avoid gastric breakdown.

In another embodiment, the present invention provides a method for screening a substance for its effectiveness in reducing the colitis-inducing effect of IL-12 comprising obtaining an animal having an established colitis; administering the substance to an animal; and assaying the animal for an effect on IL-12 which results in a reduction of the inflammatory response of the colitis, an amount of reduction of the inflammatory response greater than the amount of reduction resulting from by the administration of antibodies against IFN-γ, TNF-α or other cytokines or from the administration of cytokines themselves indicating an effective substance. A substance effective in reducing the inflammatory response of an established colitis is one that reduces or reverses the histological and clinical manifestations of the inflammation, as described above.

The ability of a substance to reduce the colitis inducing effect of IL-12 can be determined by evaluating the histological and clinical manifestations, as set forth above, of the animal with colitis before and after administration of the substance of interest and quantitating the amount of reduction of the inflammation. If the amount of reduction of the inflammatory response induced by IL-12 measured in an animal after administration of the substance is greater than the amount of reduction of the inflammatory response induced by IL-12 measured in an animal after the administration of antibodies against IFN-γ, TNF-α or other cytokines or by the administration of cytokines themselves, the substance is determined to be effective in reducing the inflammatory response of an established colitis.

The animal in which the colitis is produced can be any mammal and can include but is not limited to mouse, rat, guinea pig, hamster, rabbit, cat, dog, goat, monkey, and chimpanzee. The colitis can be produced in the animal by any method known in the art. For example, the colitis can be produced by introducing into the colon of the animal an effective amount of a hapten reagent. The hapten reagent can be, but is not limited to, 2,4,6-trinitrobenzene sulfonic acid, 2,4-dinitrochlorobenzene and other trinitrophenylamine compounds To evaluate the efficacy of anti-IL-12 treatment in humans with IBD, the following studies can be performed. Patients with active inflammation of the colon and/or the terminal ileum who have failed standard prednisone therapy (parenterally or orally) for control of the IBD can be selected. Drug efficacy can be monitored via colonoscopy. Patients can be randomized to two different protocols. In one protocol, subjects can remain on initial steroid dosage and in the second protocol, subjects can have their steroid dosage tapered after receiving anti-IL-12 therapy.

Treatment can consist of either a single dosage of 10 mg to 20 mg/kg of body weight of antibodies to IL-12 infused over a two hour period or a weekly dosage of 10 mg to 20 mg/kg of body weight of antibodies to IL-12 infused each time over a two hour period until symptoms of colitis subside. The blood pressure, pulse and temperature of the subjects can be monitored prior to and at 30 minute intervals during the two hour infusion period. Subjects can be given a laboratory evaluation consisting of a complete blood count (CBC) with differential, platelet count, SMA-18 chemistry profile, erythrocyte sedimentation rate (ESR) and a C-reactive protein assay at 1) the time of anti-IL-12 infusion; 2) 24 hours after infusion; 3) 72 hours after infusion; 4) two weeks after the last infusion; 5) four weeks after the last infusion; (6) six weeks after the last infusion; and 7) eight weeks after the last infusion.

Subjects can also undergo routine colonoscopy with video surveillance at the time of the infusion of anti-IL-12 and again at two, four, six and eight weeks after the last infusion.

Additionally, serum samples from the subjects can be assayed by ELISA for IFN-γ levels to monitor drug efficacy. Also, tissue biopsy samples obtained during colonoscopy can be cultured and assayed for IFN-γ levels.

In another embodiment, the present invention provides a method for screening a substance for its effectiveness in preventing inflammatory bowel disease comprising administering the substance to an animal susceptible to colitis; subjecting the animal to a treatment that will induce a colitis; assaying the animal for the development of a colitis; and comparing the effectiveness of the substance in preventing development of a colitis to the effectiveness of antibodies to interferon-gamma or tumor necrosis factor-alpha in preventing development of a colitis, a substance more effective in preventing the development of a colitis than antibodies to interferon-gamma or tumor necrosis factor-alpha indicating an effective substance.

Substances found to be effective in preventing IBD, such as antibodies to IL-12, can be administered to a subject to prevent the development of colitis, according to the protocols for administration described herein.

The present invention is more particularly described in the following examples which are intended as illustrative only since numerous modifications and variations therein will be apparent to those skilled in the art.

EXAMPLES

Example I. Materials, Antibodies and Cells

Reagents and Monoclonal Antibodies.

Unconjugated and biotinylated monoclonal rat anti-mouse IL-2 (clones JES6-1A12/JES6-5H4), IL-4 (BVD4-1D11/ BVD6-24G2), IL-10 (JES5- 2A5/ SXC-1), and IFN-γ R4-6A2/XMG1.2) antibodies and recombinant mouse IL-2 (specific activity: $2.5 \times 10^6$ Biological Response Modifiers Program (13RMP) units/ mg), IL-4 ($1 \times 10^7$ units/ mg by CTLL-2.4 assay), IL-10 ($5 \times 10^5$ units/ mg) and IFN-γ ($1 \times 10^7$ units/ mg) were purchased from Pharmingen and Genzyme Corp., (Cambridge, Mass.) respectively. Purified hamster anti-mouse CD3ε (clone 145-2C11) and hamster anti-mouse CD28 (clone 37.51) antibodies were obtained from Pharmingen.

Cell isolation and purification of lamina propria CD4+T cells (LP cells).

LP cells were isolated from freshly obtained colonic specimens using a modification of the technique described by van der Heijden and Stok (17). After removal of the Peyer's patches, the colon was washed in Hanks Balanced Saline Solution-calcium and magnesium free (HBSS-CMF), cut into 0.5 cm pieces and incubated twice in HBSS containing disodium ethylenediaminetetraacetate (EDTA) (0.37 mg/ ml) and dithiothreitol (DTT) (0.145 mg/ ml) at 37° C. for 15 min. The tissue was digested further in RPMI 1640 medium (Whittaker, Walkersville, Md.) containing Collagenase D (400 U/ml) and DNase I (0.1 mg/ ml) (Boehringer Mannheim, Indianapolis, Ind.) in a shaking incubator at 37° C. LP cells were then layered on a 40%–100% Percoll gradient (Pharmacia, Uppsala, Sweden) and lymphocyte-enriched populations were isolated from the cells at the 40–100% interface. Enriched CD4+ T cell populations were obtained by negative selection using mouse CD4+T cell isolation columns (Isocell; Pierce Co., Rockford, Ill.). The resultant cells, when analyzed by flow cytometry (FACScan; Becton Dickinson, Sunnyvale, Calif.), consisted of greater than 85% CD4+ cells.

Cell culture of LP cells.

Cell cultures of LP cells were performed in complete medium consisting of RPMI-1640 medium supplemented with 3 mM L-glutamine, 10 mM HEPES buffer, 10 μg/ml gentamycin (Whittaker), 100 U ml each of penicillin and streptomycin (Whittaker), 0.05 mM 2-mercaptoethanol (2ME) (Sigma Chemical, St Louis, Mo.) and 10% FCS.

Isolation of spleen CD4+ T cells.

Spleens were aseptically removed and subsequently digested with collagenase (400 U/ ml) and DNase I (12.5 μg/ml) at 37° C. for 15 minutes. After filtration straining, the resulting splenocyte suspension was depleted of red blood cells (RBC) by hypotonic lysis with ammonium chloride-Tris (ACK) lysing buffer (B & B Scott, W. Warwick, R.I.). Cells collected from the 70%/90% layer of a Percoll-gradient centrifugation underwent further negative selection using mouse CD4+ T cell isolation columns. As assessed by fluorescence activated cell sorter (FACS) analysis, the resulting cell population contained more than 85% CD4+ cells.

Cell culture of spleen CD4+ T cells.

$10^5$ spleen CD4+ T cells were cultured in 1 ml of complete medium. Culture supernatants were removed after 48 hours and assayed for cytokine concentration as described above.

Example II. Treatment of mice with anti-IL-12 antibodies

Treatment with anti-IL-12 antibodies.

The hybridoma cell line (C17.8) producing neutralizing rat anti-mouse IL-12 antibody (G. Trinchieri The Wistar Institute, Philadelphia, Pa. (20, 21)) was used to generate ascites fluid in nude mice according to standard procedures and antibodies were purified using E-Z-SEP purification kits (Middlesex Sciences, Inc, Foxborough, Mass.). Rat control IgG was obtained from Jackson Immuno Research (West Grove, Pa.). One mg of either rat anti-mouse IL-12 antibodies or rat control IgG was administered intraperitoneally into mice pretreated with TNBS at various time points.

Example III. Induction and evaluation of colitis

Induction of colitis.

Specific pathogen-free 2–4 month old female BALB/c or SJL/J mice were obtained from the National Cancer Institute (NC, Bethesda, Md.) and maintained in the building 10A animal facility at the National Institutes of Health. The mice were lightly anesthetized with metofane (methoxyflurane; Pitman-Moore, Mundelein Ill.). A 3.5 F catheter was inserted into the colon until the tip was 4 cm proximal to the anus. To induce colitis, 0.5 mg of the hapten reagent 2,4,6-trinitrobenzene sulfonic acid (TNBS; Sigma, St. Louis, Mo.) in 50% ethanol (to break the intestinal epithelial barrier) was slowly administered into the lumen of the colon via the catheter fitted onto a 1 ml syringe. In control experiments, mice received 50% ethanol alone using the same technique described above. The total injection volume was 100 μl in both groups, allowing TNBS or ethanol to reach the entire colon including caecum and appendix. Animals were kept in a vertical position for 30 seconds and returned to their cages.

Grading of histologic changes.

Tissues were removed at various time points and embedded in paraffin. Paraffin sections were made and stained with haematoxylin and eosin. The degree of inflammation on microscopic cross sections of the colon was graded semi-quantitatively from 0 to 4 [0—no signs of inflammation, colon is indistinguishable from that of a normal colon; 1—very low level of leucocytic infiltration (1–10% of field infiltrated with leucocytes); 2—low level of leucocytic infiltration (11–25% of field infiltrated with leucocytes), hyperemia; 3—high level of leucocytic infiltration (26–50% of field infiltrated with leucocytes), high vascular density, thickening of the colon wall; 4–transmural leucocytic infiltrations (>50% of field infiltrated with leucocytes), loss of goblet cells, high vascular density, thickening of the colon wall]. Grading was done in a blinded fashion by the same pathologist.

Morphometric assessment of colon wall thickness.

Three or more animals from each treatment group were randomly selected at various time points and colon samples were removed and embedded in paraffin. Thickness of the colon wall was determined on cross sections by measuring the distance from the serosal surface to the luminal surface at 2 mm intervals along the entire length of each section through a calibrated eyepiece using an Olympus Vanox SI microscope.

Immunohistochemistry.

Samples were put into optimal cutting temperature (OCT) -compound on dry ice and 7 µm cryo-sections were cut according to standard procedures. Sections were then air dried and fixed in cold acetone for 2 min at room temperature. Samples were rehydrated in phosphate buffered saline (PBS) for 15 min, blocked with 5% fetal calf serum (FCS) in PBS for 20 min and incubated with fluorescein isothiocyanate (FITC)- conjugated rat anti-mouse CD4 antibody (1: 100 dilution; Pharmingen, San Diego, Calif.) for 45 min in a dark humid chamber. Sections were then washed for 15 min in PBS, mounted and analyzed with a fluorescence microscope at excitation wavelength of 490 nm.

Quantification of CD4+ T lymphocytes was performed on cryostat sections for at least three specimens from each time point and each treatment group by examining ten randomly selected high power fields (HPF). Under these experimental conditions (x400 magnification), one HPF represented 0.25 mm$^2$.

Intrarectal administration of 2,4,6-trinitrobenzene sulfonic acid induces a chronic granulomatous colitis in BALB/c and SJL/J mice.

BALB/c and SJL/J mice subjected to intrarectal administration of TNBS in 50% ethanol reproducibly developed pancolitis with severe diarrhea and rectal prolapse accompanied by an extensive wasting disease. The peak of clinical disease occurred at three weeks and clinical signs of colitis usually subsided after two months. Control mice treated with 50% ethanol alone failed to develop wasting disease and appeared healthy.

The colons of TNBS-treated BALB/c mice removed seven days after administration of TNBS revealed striking hyperemia and inflammation, whereas the colons of control mice treated with 50% ethanol alone showed no macroscopic signs of inflammation. In addition, TNBS-treated mice displayed splenomegaly.

Histologic analysis during the first days after induction of colitis showed infiltrations of neutrophil granulocytes into the colon. At day 7 a transmural inflammation affecting the entire colon (but sparing the small bowel) was found. The colitis was mainly characterized by lymphocytic infiltrates that were associated with thickening of the colon wall, ulcerations, loss of goblet cells and the presence of granulomas. Immunohistochemical staining showed that on day 7, CD4+ T cells were increased in colons of TNBS-treated mice compared to control mice. The differences in inflammatory activity were further confirmed by histologic grading of the colon sections. (FIG. 1). As assessed by morphometric analysis of colon wall thickness and number of CD4+ T lymphocytes (Table 1), disease intensity usually peaked between two and four weeks after administration of TNBS. At later stages of the disease there was reduction in the number of granulocytes but intramural lymphoid aggregates persisted and beginning fibrosis was found. These histological signs of inflammation were still detected two months after TNBS-treatment, but were absent in ethanol-treated mice.

Histologically, the spleens of TNBS-treated mice showed an increase in the size of the red pulp and the periarteriolar lymphoid sheaths at day 7 when compared with spleens from control mice. Fluorescence-activated cell sorter (FACS) analysis of spleen lymphocytes revealed a two-fold increase in the percentage of CD4+ and CD8+ T cells in TNBS-treated mice compared with control ethanol-treated mice and normal BALB/c mice along with a reduction in B220+ B cells.

Early administration of antibodies to IL-12 represses colitis and abolishes wasting disease in TNBS-treated mice.

To determine if antibodies to IL-12 might influence disease activity, mice were treated five and nine days after induction of the colitis systemically with anti-IL-12 or control rat IgG. When mice were treated with anti-IL-12, a striking improvement of the wasting disease became apparent. Anti-IL-12 treated mice became more active and lost their ruffled coat appearance when compared with untreated mice or mice given control rat IgG. In addition, mice administered anti-IL-12 usually obtained their initial body weight, whereas control IgG- treated mice continued to lose weight. Finally, gross inspection of the colon at day 12 revealed reduction in inflammatory activity in animals administered anti-IL-12.

Figure 2:
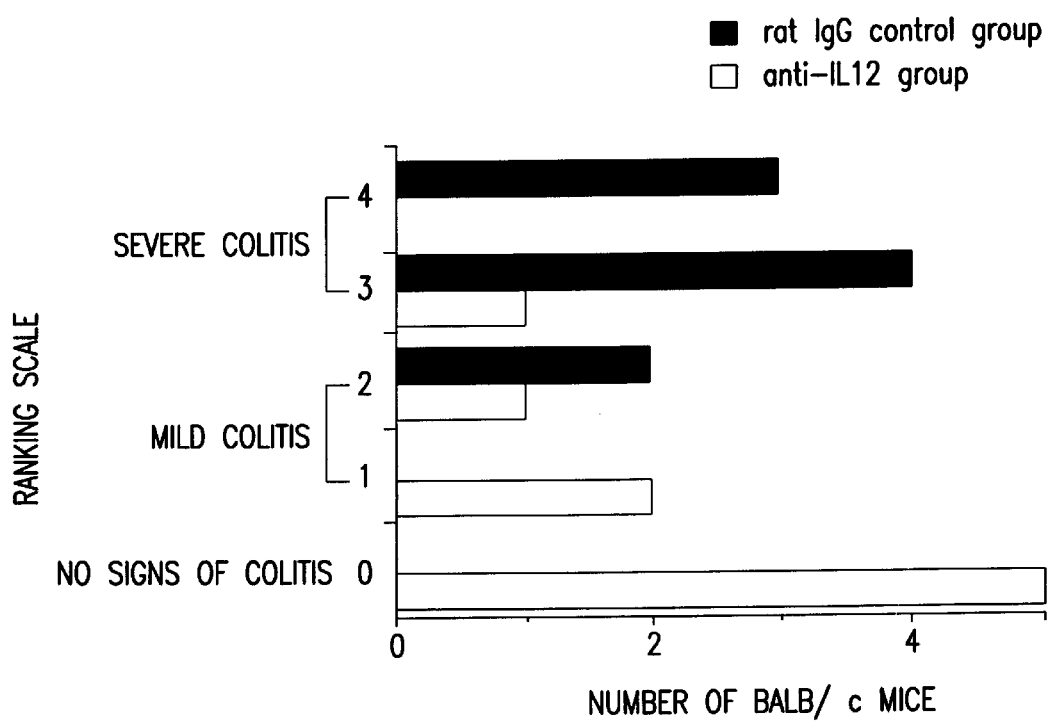
FIG. 2 shows the results of the histologic grading of colon sections from BALB/c mice treated with TNBS and antibodies to IL-12 (open bars) and from mice treated with TNBS and rat control IgG (solid bars). Colon specimens were taken at indicated time points after administration of TNBS or ethanol and the magnitude of inflammatory changes in the colons was analyzed on HE-stained cross colon sections. Data were pooled from three independent experiments in each group.

Histologic studies showed significantly fewer inflammatory cells in the colons of anti-IL-12 treated mice. In most cases, anti- IL-12 treatment completely abrogated the TNBS-induced inflammation and restored a normal histologic appearance of the colon. This was confirmed by histologic grading of colon sections; pooled data from three independent experiments showed significant reduction in inflammatory activity after anti-IL- 12 treatment (FIG. 2).

Example IV. Cytokine Assays

ELISA.

To measure cytokine production, 24-well plates (Costar, Cambridge, Mass.) were coated with 10 µg/ml murine anti-CD3ε antibody in carbonate buffer (pH 9.6) overnight at 4° C. 10$^5$ LP T cells were cultured in 1 ml of complete medium in precoated or uncoated wells and 1 µg/ml soluble anti-CD28 antibody was added to the anti-CD3ε coated wells. Culture supernatants were removed after 48 hours and assayed for cytokine concentration. Cytokine concentrations were determined by specific ELISA as per manufacturer's recommendation (Pharmingen) using Immulon-4 96-well microtiter plates (Dynatech Laboratories Inc., Chantilly, Va.). Optical densities were measured on a Dynatech MR 5000 ELISA reader at a wavelengh of 490 nm.

StimulatedLP cells of TNBS-treated mice secrete Th1 cytokines.

To examine cytokine production by infiltrating LP cells in the colons of TNBS-treated mice, this cell population was purified from colonic tissue specimens seven days after the induction of colitis and the cytokine pattern of these cells was compared with that of LP cells obtained from colonic tissue specimens of control ethanol-treated mice. Cells were cultured for two days and culture supernatants were analyzed for concentration of Th1 (IL-2, IFN-γ) and Th2 (IL-4, IL-I 0) cytokines by specific ELISA. A ten-fold increase in the spontaneous IFN-γ production by LP cells was found in TNBS-treated mice. Furthermore, LP cells from TNBS-treated mice stimulated with anti-CD3 and anti-CD28 produced 20 to 50-fold higher levels of IL-2 and IFN-γ than LP cells from control mice. Similarly, an increase in the spontaneous (4.5 U vs. 1.8 U) and induced (46 U vs. 16.8 U after stimulation with anti-CD3 and anti-CD28) IFN-γ production by spleen CD4+ T cells was found in the TNBS-treated animals compared with the ethanol control group at this time point.

In contrast to the above finding, secretion of IL-4 by unstimulated LP cells from TNBS-treated mice was identical compared to LP cells from ethanol-treated control mice. In stimulated LP cells from TNBS-treated mice, average secretion of IL-4 was reduced about five-fold compared with ethanol-treated control mice. Finally, the secretion of IL-10 by stimulated and unstimulated LP cells was similar in TNBS- and ethanol-treated mice.

In situ reverse transcriptase polymerase chain reaction (RT-PCR).

In situ RT-PCR for IFN-γ mRNA expression was performed as previously described (18). Cryosections were placed on charged glass slides cut to fit into 0.5 ml Eppendorf tubes. Samples were fixed in 10% formaldehyde overnight at 4° C., washed three times in PBS and four times in autoclaved $dH_2O$ for 5 min. Sections were permeabilized with 2 mg/ml trypsinogen (Sigma) in 0.01N HCl for 15 min at 25° C., followed by neutralization with buffer A (0.1M Tris HCl (pH 7.5), 0.1M NaCl). For DNA degradation, the sections were incubated in RQ1 RNase-free DNase (8 U/100 ml; obtained from Promega, Madison, Wis.) in buffer B containing 40 mM Tris HCl (pH 7.9), 10 mM NaCl, 6 mM $MgCl_2$ and 0.1 mM $CaCl_2$ at 37° C. for 12 min and at 75° C. for 10 min. Next, sections were incubated for 60 min at 50° C. in a Perkin Elmer Thermocycler in 100 μl of the following reaction mixture: 10 mM Tris HCl, 50 mM KCl, 1.5 mM $MgCl_2$, 25 μM dATP, 25 μM dTTP, 25 μM dCTP, 25 μM dGTP (Pharmacia, Piscataway, N.J.), 100 nM of either IFN-γ primer (sense: 5'-GACAATCAGG CCATCAGCAACAAC-3' (SEQ ID NO:1); antisense primer: 5'-TCCTGAGGCTGGATTCCGGCAACA-3' (SEQ ID NO:2) (19)), 10 mM DTT, 75 U RNasin, and 400 U M-MLV reverse transcriptase (Gibco BRL, Gaithersburg, Md.). Slides were washed five times each in sodium citrate buffer (3M NaCl, 0.3M $Na_3$Citrate, pH 7.0, 2×SSC), 1×SSC, 0.5×SSC, and twice in dH2O.

The polymerase chain reaction (PCR) method was carried out in situ for either sense- or antisense-primed cDNA in 100 μl of the following reaction mixture: 25 μM of each the nucleotides dATP, dCTP, dGTP and 23.7 μM dTTP, 1.25 μM digoxigenin-11-dUTP (dig-11-dUITP; obtained from Boehringer Mannheim), 10 mM Tris HCl, 50 mM KCl, 1.5 mM $MgCl_2$, 5 U Taq polymerase (Boehringer) and 10 nM of IFN-γ primers. After denaturation of the samples for 4 min at 95° C., thermocycling was performed for five cycles (94° C. for 70 sec, 62° C. for 1 min, 72° C. for 1 min); the final extension was done for 10 min at 72° C. The samples were then washed in SSC solutions (2×SSC, 1×SSC, 0.5×SCC; 5 times each) and immunodetection was performed using the DIG nucleic acid detection kit (Boehringer Mannheim). Sections were dehydrated in graded ethanols, placed in xylene and mounted on coverslips.

Elispot assay for IFN-γ.

$10^5$ LP cells were incubated for one day in anti-CD3ε-coated 24 well-plates and 1 μg/ml soluble anti-CD28 antibody was added. Cells were incubated in 24 well-plates that were coated with rat anti-mouse IFN-γ (Pharmingen). After 12 hours, plates were washed in PBS/ Tween and biotinylated rat anti-mouse IFN-γ (Pharmingen) (2 μg/ml) was added. Plates were incubated overnight at 4° C. After washing in PBS/ Tween, streptavidin-alkaline phosphatase (1: 1000 dilution; obtained from Zymed) was added for 30 min at 37° C. Plates were washed again in PBS/ Tween and the alkaline phosphatase (AP) substrate (Promega, Madison, Wis.), together with 1% agarose gel, was added. Color reaction was allowed to proceed for 24 hours before spots were photographed.

In situ polymerase chain reaction studies show elevated IFN-γ mRNA expression in the colons of TNBS-treated BALB/c mice.

To determine if the observed increase in IFN-γ production was also observed at the mRNA level, the mRNA expression of IFN-γ in the colon of TNBS-treated mice was evaluated by in situ PCR studies. Ethanol-control treated animals did not show significant expression of IFN-γ mRNA at day 7. In the TNBS-treated animals, however, a dramatic upregulation of IFN-γ mRNA expression at the same time point was observed. High staining intensity was seen particularly in the subepithelial areas.

IFN-γ production by stimulated LP cells is abolished in TNBS-treated mice given anti-IL-12.

An analysis of IFN-γ production by LP cells in anti-IL-12 treated animals revealed an abrogation of IFN-γ production in TNBS-treated mice administered anti-IL-12 compared with rat IgG-treated mice, indicating that the anti-IL-12 treatment can act by influencing the Th1-like response of local CD4+ T cells. In addition, Elispot assays for IFN-γ secretion by LP cells showed a dramatic reduction in the average number of Elispots in the anti-IL-12 treated group compared to the rat control IgG-treated group. The size of the Elispots, however, was similar in both groups, indicating that the reduction in IFN-γ secretion by LP cells from anti-IL-12 treated mice was mainly due to a reduction in the number of IFN-γ secreting cells.

Late administration of antibodies to IL-12 abolishes wasting disease in mice with TNBS-induced colitis.

To determine if anti-IL-12 treatment would be effective during later phases of the disease when colitis was fully established, administration of anti-IL-12 or control rat IgG was started on day 20 and repeated on days 24 and 28. A striking increase in the average weight of mice was found after anti-IL-12 treatment but not after rat control IgG treatment. Furthermore, when LP cells from such mice were stimulated with anti-CD3 and anti-CD28, an abrogation of IFN-γ secretion was observed in those mice given anti-IL-12 but not those given rat control IgG.

Example V. Treatment of humans with anti-IL-12 antibodies

Administration of antibodies to IL-12 to a human subject diagnosed with an established colitis.

To inhibit the colitis-inducing effect of IL-12 in a human subject, 10 mg to 20 mg/kg of body weight of antibodies to IL-12 can be administered parenterally as a single dose administered over a two hour period or as weekly infusions administered over a two hour period until the symptoms of colits, such as abdominal pain, diarrhea, dehydration or other common symptoms of IBD subside. For oral administration, 500 to 1000 mg of antibodies to IL-12 can be administered P.O. in a single dose or in weekly doses until the symptoms of colitis, as described above, subside.

Example VI. Humanized antibodies

Production of humanized mouse antibodies to IL-12.

Rodent monoclonal or polyclonal antibodies can be modified according to the protocols set forth in Junghans et al. (25), Brown et al. (26) and Kettleborough et al. (27). Specifically, rodent antibodies can be modified for human administration by constructing, through recombinant DNA protocols known to one of skill in the art, a chimeric rodent-human antibody composed of rodent variable regions and human heavy and light chain constant regions. Another approach to humanizing rodent antibodies is to graft rodent complementarity-determining regions (CDRs) from the rodent variable regions into human variable regions. By using either of these approaches, rodent antibodies can be humanized for administration into human subjects.

Example VII. Methods for screening substances in an animal model

Screening a substance for its effectiveness in reducing the inflammatory response of an established colitis.

To determine if a substance is effective in reducing the inflammatory response of an established colitis by reversing the colitis-inducing effect of IL-12, an animal model for established colitis can be prepared according to the protocol set forth in Example III, above. An amount of the substance of interest can then be administered to the animal parenterally in a dosage regimen consisting of 1 mg in a single dose or a weekly regimen of 1 mg twice a week. At designated time points after administration of the substance to the animal, the amount of reduction of the inflammatory response can be determined according to the protocols set forth in Example III, above. Antibodies to IFN-γ and antibodies to TFN-α can also be administered to animals in which colitis has been established in a dosage regimen consisting of 1 mg in a single dose or a weekly regimen of 1 mg twice a week. At designated time points after administration of the anti-IFN-γ or TNF-α, the amount of the reduction of the inflammatory response can be determined according to the protocols set forth in Example III, above. A substance that reduces the inflammatory response of the colitis to a greater degree than the amount of reduction of the inflammation induced by anti-IFN-γ or anti-TNF-α administration is considered to be an effective substance for treating an established colitis.

Screening a substance for its effectiveness in preventing IBD.

To determine if a substance is effective in preventing IBD, the substance can be administered to an animal susceptible to colitis and the animal can then be subjected to a treatment that will induce colitis (e.g., by treatment with a hapten reagent, as described in the Examples herein). An amount of the substance of interest can be administered to the animal parenterally in a dosage regimen consisting of 1 mg in a single dose or a weekly regimen of 1 mg twice a week. At designated time points after administration of the substance to the animal and treatment of the animal to induce colitis, the development of an inflammatory response can be determined according to the protocols set forth in Example III, above. Antibodies to IFN-γ and antibodies to TNF-α can also be administered to animals which are susceptible to colitis in a dosage regimen consisting of 1 mg in a single dose or a weekly regimen of 1 mg twice a week. At designated time points after administration of the anti-IFN-γ or TNF-α and treatment of the animal to induce colitis, the development of an inflammatory response can be determined according to the protocols set forth in Example III, above. A substance that prevents the inflammatory response to a greater degree than the degree of prevention of the inflammation induced by anti-IFN-γ or anti-TNF-α administration is considered to be an effective substance for preventing IBD.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties, as well as the references cited in these publications, are hereby incorporated by reference into this application in order to more fully describe the state of the art to which this invention pertains.

TABLE 1

Assessment of colon wall thickness and number of CD4+ T lymphocytes per high power field (HPF) in the colons of TNBS- and ethanol-treated BALB/c mice at different time points after treatment. Colon wall thickness is expressed in micrometers ± SEM. The values for CD4+ T lymphocytes reported are expressed as positive cells per HPF ± SEM.

| Weeks After Treatment | Colon Wall Thickness ($\mu$m) | | CD4+ T lymphocytes per HPF | |
|---|---|---|---|---|
| | Ethanol-treated Mice | TNBS-treated Mice | Ethanol-treated Mice | TNBS-treated Mice |
| 0 | 226.4 ± 12.5 | 210.4 ± 20.8 | 3.7 ± 0.4 | 3.7 ± 0.4 |
| 1 | 239.8 ± 6.0 | 419.8 ± 38.9 | 5.1 ± 0.5 | 38.9 ± 4.1 |
| 2 | 213.0 ± 8.5 | 522.2 ± 76.2 | 4.7 ± 0.6 | 58.2 ± 4.1 |
| 4 | 213.0 ± 8.6 | 427.5 ± 56.3 | 3.7 ± 0.4 | 76.1 ± 6.4 |
| 6 | 219.3 ± 16.0 | 394.2 ± 45.0 | 4.3 ± 0.5 | 34.4 ± 3.3 |
| 8 | 238.8 ± 7.4 | 412.2 ± 26.9 | 5.4 ± 0.5 | 29.0 ± 3.7 |

REFERENCES

1. Podolsky, D. K. 1991. Inflammatory bowel disease. *New Engl. J. Med* 325:928–937.

2. Strober, W., and M. F. Neurath. 1995. Immunological diseases of the gastrointestinal tract. in: R. R. Rich (ed) *Clinical Immunology-Principles and Practice,* Chapter 94. Mosby, St. Louis. 1401–1428.

3. Strober, W., and R. O. Ehrhardt. 1993. Chronic intestinal inflammation: an unexpected outcome on cytokine or T cell receptor mutant mice. *Cell* 75:203–205.

4. Hammer, R. E., S. D. Maika, J. A. Richardson, Y. P. Tang, and J. D. Taurog. 1990. Spontaneous inflammatory disease in transgenic rats expressing HLA-B27 and human β2m: an animal model of HLAB-27 - associated human disorders. *Cell* 63:1099–1112.

5. Sadlack, B., H. Merz, H. Schorle, A. Schimpl, A. C. Feller, and I. Horvak. 1993. Ulcerative colitis-like disease in mice with a disrupted interleukin-2 gene. *Cell* 75:253–261.

6. Kühn, R., J. Löhler, D. Rennick, K. Rajewsky, and W. Müller. 1993. Interleukin-10-deficient mice develop chronic enterocolitis. *Cell* 75:263–274.

7. Mombaerts, P., E. Mizoguchi, M. J. Grusby, L. H. Glimcher, A. K. Bahn, and S. Tonegawa. 1993. Spontaneous development of inflammatory bowel disease in T cell receptor mutant mice. *Cell* 75:275–282.

8. Powrie, F., M. W. Leach, S. Mauze, S. Menon, L. B. Caddie, and R. L. Coffman. 1994. Inhibition of Th1 responses prevents inflammatory bowel disease in scid mice reconstituted with CD45RBhi CD4+ T cells. *Immunity* 1:553–562.

9. Kobayashi, M., L. Fitz, M. Ryan, R M. Hewick, S. C. Clark, S. Chan, R. Loudon, F. Sherman, B. Perussia, and G. Trinchieri. 1989. Identification and purification of natural killer cell stimulatory factor (NKSF), a cytokine with multiple biological effects on human lymphocytes. *J. Exp. Med* 170:827–845.

10. Seder, R. A., R. Gazzinelli, A. Sher, and W. E. Paul. 1993. IL-12 acts directly on CD4+ T cells to enhance priming for IFN-γ production and diminishes IL-4 inhibition of such priming. *Proc. Natl. Acad Sci.* USA 90:10188–10192.

11. Ling, P., M. K. Gately, U. Gubler, A. S. Stern, P. Lin, K. Hollfelder, C. Su, Y.-C. E. Pan and J. Hakimi. 1995. Human IL-12 p40 homodimer binds to the IL-12 receptor but does not mediate biologic activity. *J. Immunol* 154:116–127.

12. Podlaski, F. J., V. B. Nanduri, J. D. Hulmes, Y.-C. E. Pan, W. Levin, W. Danho, R. Chizzonite, M. K. Gately, and A. S. Stern. 1992. Molecular characterization of interleukin 12. *Arch. Biochem. Biophys.* 294:230–237.

13. Kubin, M., M. Kamoun, and G. Trinchieri. 1994. Interleukin 12 synergizes with B7/CD28 interaction in inducing efficient proliferation and cytokine production of human T cells. *J. Exp. Med* 180:211–222.

14. Wynn, T. A., I. Eltoum, I. P. Oswald, A W. Cheever, and A. Sher. 1994. Endogenous interleukin 12 (IL-12) regulates granuloma formation induced by eggs of Schistosoma mansoni and exogenous IL-12 both inhibits and prophylactically immunizes against egg pathology. *J. Exp. Med* 179:1551–1561.

15. Murray, H. W., and J. Hariprashad. 1995. Interleukin 12 is effective treatment for an established systemic intracellular infection: experimental visceral leishmaniasis. *J Exp. Med* 181:387–391.

16. Leonard, J. P., K. E. Waldburger, and S. J. Goldman. 1995. Prevention of experimental autoimmune encephalomyelitis by antibodies against interleukin 12. *J. Exp. Med* 181:381–386.

17. Van der Heijden, P. J., and W. Stok. 1987. Improved procedure for the isolation of functionally active lymphoid cells from the murine intestine. *J. Immunol. Meth.* 103:161–167.

18. Heniford, B. W., A. Shum-Siu, M. Leonberger, and F. J. Hendler. 1993. Variation in cellular EGF receptor mRNA expression demonstrated by in situ reverse transcriptase polymerase chain reaction. *Nucleic AcidRes.* 21:3159–3166.

19. Gray, P. W., and D. V. Goeddel. 1983. Cloning and expression of murine immune interferon cDNA. *Proc. Natl. Acad Sci.* U.S.A. 80:5842–5846.

20. Wysocka, M., M. Kubin, L. Q. Vieira, L. Ozmen, G. Garotta, P. Scott, and G. Trinchieri. 1995. Interleukin-12 is required for interferon-γ production and lethality in LPS-induced shock in mice. *Eur. J. Immunol.* 25:672–676.

21. Trinchieri, G. 1994. Interleukin-12: a cytokine produced by antigen- presenting cells with immunoregulatory functions in the generation of T-helper cells type 1 and cytotoxic lymphocytes. *Blood* 84:4008–4027.

22. Eldridge et al. 1989. *Cur. Topics in Microbiol. andimmunol.,* 146:59–65.

23. Harlow and Lane, *Antibodies; A Laboratory Manual,* Cold Spring Harbor Laboratory, Cold Spring Harbor, N.Y., (1988).

24. Martin, E. W. *Remington's Pharmaceutical Sciences,* Martin, latest edition, Mack Publishing Co., Easton, Pa.

25. Junghans et al. 1990. *Cancer Research* 50:1495–1502.

26. Brown et al. 1991. *Proc. Natl. Acad Sci.* USA 88:2663–2667.

27. Kettleborough et al. 1991. *Protein Engineering* 4:773–783.

28. Oka et al. 1990. *Vaccine,* 8:573–576.

29. Van DuFleman et al. 1995. Treatment of Crohn's Disease with Anti-Tumor Necrosis Factor Chimeric Monoclonal Antobody (cA2). *Gastroenterology* 109:129–135.

What is claimed is:

1. A method for treating the inflammatory response of an established colitis in a human subject with inflammatory bowel disease, comprising administering to a subject diagnosed with an established colitis from an inflammatory bowel disease an amount of an antibody to interleukin-12 effective in reducing the colitis-inducing effect of interleukin-12, thereby treating the inflammatory response of an established colitis.

2. A method for screening a substance for its effectiveness in reducing the colitis-inducing effect of interleukin-12 in an established colitis comprising:

a) obtaining an animal having an established colitis;
   b) administering the substance to an animal; and
   c) assaying lamina propria cells from the animal for an amount of secretion of interferon-gamma, whereby a decrease in the amount of interferon-gamma secreted by the lamina propria cells of the animal as compared to the amount of interferon-gamma secreted by lamina propria cells of a control animal having an established colitis and without having the substance administered indicates the substance is effective in reducing the colitis-inducing effect of interleukin-12 in an established colitis.

3. The method of claim 2, wherein an amount of secretion of interferon-gamma by lamina propria cells is assayed according to a method selected from the group consisting of ELISA, reverse transcriptase-polymerase chain reaction and ELISPOT.

4. The method of claim 2, wherein the animal has an established colitis produced by introducing into the colon of the animal an effective amount of a hapten reagent.

5. The method of claim 4, wherein the hapten reagent is 2,4,6-trinitrobenzene sulfonic acid.

6. The method of claim 2, wherein the animal is a mouse.

7. A method for screening a substance for its effectiveness in preventing the development of a colitis by inhibiting the colitis-inducing effect of interleukin-12 comprising:

a) administering the substance to an animal susceptible to colitis;
   b) subjecting the animal to a treatment that will induce a colitis; and
   c) assaying the lamina propria cells of the animal for an amount of secretion of interferon-gamma, whereby a lack of increase in the amount of interferon-gamma secreted by the lamina propria cells of the animal as compared to an increase in the amount of interferon-gamma secreted by lamina propria cells of a control animal susceptible to colitis and subjected to the treatment and without having the substance administered indicates the substance is effective in preventing the development of a colitis by inhibiting the colitis-inducing effect of interleukin-12.

8. The method of claim 7, wherein an amount of secretion of interferon-gamma by lamina propria cells is assayed according to a method selected from the group consisting of ELISA, reverse transcriptase-polymerase chain reaction and ELISPOT.

9. The method of claim 7, wherein the animal is a mouse.

10. The method of claim 7, wherein the treatment that will induce a colitis is the introduction of an effective amount of a hapten reagent into the colon of the animal.

11. The method of claim 10, wherein the hapten reagent is 2,4,6-trinitrobenzene sulfonic acid.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

G A C A A T C A G G    C C A T C A G C A A    C A A C          2 4

( 2 ) INFORMATION FOR SEQ ID NO:2:

( i ) SEQUENCE CHARACTERISTICS:

( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCCTGAGGCT GGATTCCGGC AACA 24